(12) United States Patent
Madden

(10) Patent No.: US 8,026,077 B2
(45) Date of Patent: Sep. 27, 2011

(54) PROTEIN KINASE C GAMMA AS A BIOMARKER FOR NEUROPSYCHOLOGICAL AND COGNITIVE FUNCTIONS IN THE CENTRAL NERVOUS SYSTEM

(76) Inventor: Kathleen S. Madden, Bethesda, MD (US)

( * ) Notice: Subject to any disclaimer, the term of this patent is extended or adjusted under 35 U.S.C. 154(b) by 536 days.

(21) Appl. No.: 12/020,348

(22) Filed: Jan. 25, 2008

(65) Prior Publication Data

US 2008/0187939 A1    Aug. 7, 2008

Related U.S. Application Data

(60) Provisional application No. 60/886,532, filed on Jan. 25, 2007.

(51) Int. Cl.
*G01N 33/573* (2006.01)
(52) U.S. Cl. .......................................................... 435/7.4
(58) Field of Classification Search ........................ None
See application file for complete search history.

(56) References Cited

U.S. PATENT DOCUMENTS 5,186,173 A * 2/1993 Zuckerman .................... 600/329
6,268,223 B1 * 7/2001 Cornell-Bell et al. ......... 436/526

OTHER PUBLICATIONS

Gorman et al. Early evidence of a regulated response to hypoxaemia in sheep that preserves the brain cortex. Neurosci Lett. Feb. 20, 2006;394(3):174-8. Epub Nov. 21, 2005.*
Inomata et al. Elevated erythropoietin in vitreous with ischemic retinal diseases. Neuroreport. Apr. 9, 2004;15(5):877-9.*
Virues-Ortega et al. Neuropsychological functioning associated with high-altitude exposure. Neuropsychol Rev. Dec. 2004;14(4):197-224.*

* cited by examiner

*Primary Examiner* — Daniel E Kolker
*Assistant Examiner* — Gregory S Emch
(74) *Attorney, Agent, or Firm* — Novak Druce DeLuca+Quigg LLP

(57) ABSTRACT

Embodiments of the present invention are directed to a biological marker, the gamma isoform of protein kinase C (PKCg), which surprisingly allows rapid identification of compromised cognitive, behavioral, and neuropsychological functions under conditions associated with acute, transient hypoxia in humans. It was surprisingly discovered that PKCg is released from neural cells and can be detected in peripheral blood after hypoxic events unrelated to the reduction or elimination of blood flow through affected tissues. Embodiments of this invention are also directed to a broad range of clinical applications, particularly in emergency medicine. Other embodiments are related to compositions and methods for distinguishing between hypoxic encephalopathies and conditions arising from neuroanatomical/structural anomalies and/or incidental pathologies, for example, alcohol intoxication.

14 Claims, No Drawings

PROTEIN KINASE C GAMMA AS A BIOMARKER FOR NEUROPSYCHOLOGICAL AND COGNITIVE FUNCTIONS IN THE CENTRAL NERVOUS SYSTEM

REFERENCE TO RELATED APPLICATIONS

This application claims priority to U.S. Provisional Application No. 60/886,532 entitled "Protein Kinase C Gamma as a Biomarker for Neuropsychological and Cognitive Functions in the Central Nervous System," filed Jan. 25, 2007, the entirety of which is specifically and entirely incorporated by reference.

BACKGROUND

1. Field of Invention

This invention is directed to kits, compositions and methods of identifying neurological, neuropsychological, neuropsychiatric, behavioral and cognitive functions in the central nervous system, PKCg biomarkers directed to non-ischemic events.

2. Description of the Background

The events of ischemia include hypoxia and hypoglycemia due to the reduction or elimination of blood flow through affected tissues. However, hypoxia also occurs under conditions of normal or even increased cerebral blood flow.

The effects of hypoxia on central nervous system functions, such as short-term memory loss and the impairment of cognition and performance tasks have been studied through a variety of experimental approaches and models. Neurological, neuropsychological and psychometric tests have been used to assess central nervous system function. Additionally, dysfunctions of the cerebellum include cognitive affective syndrome, ataxia, and dysmetria of thought. Considerable efforts are underway to clarify the cellular and molecular mechanisms contributing to these processes. The gamma isoform of protein kinase C (PKCg) is unique to the central nervous, including the eye. Although broadly distributed throughout the brain, PKCg is concentrated in the hippocampus and cerebellum, structures associated with information processing such as learning and cognition. In ischemia, PKCg has been found in samples of peripheral blood (see U.S. Pat. No. 6,268,223); however, hypoxia occurring under conditions of normal or even increased cerebral blood flow has not heretofore been studied in detail.

Acute mountain sickness is among the most prominent pathophysiological conditions related to hypoxia at high altitudes and is characterized by a range of neurological impairments. Table 1 depicts physiological variables in healthy subjects at sea level and at high altitude. If not effectively treated, high altitude cerebral encephalopathies (HACE), a potentially lethal condition, ensue.

TABLE 1

Central Hemodynamic, Blood Gases, and Transcranial Doppler Variables in 35 Healthy Subjects at Sea Level and at High Altitude. (Cf. Van Osta)

|  | Sea Level | Altitude | P |
|---|---|---|---|
| HR, bpm | 76 ± 20 | 85 ± 12 | <0.05 |
| $Sao_2$ | 97 ± 1 | 79 ± 7 | <0.001 |
| $Pao_2$, mm Hg | 90 ± 11 | 41 ± 6 | <0.001 |
| $Paco_2$, mm Hg | 40 ± 2 | 30 ± 2 | <0.001 |
| Systolic BP, mm Hg | 137 ± 20 | 137 ± 26 | NS |

TABLE 1-continued

Central Hemodynamic, Blood Gases, and Transcranial Doppler Variables in 35 Healthy Subjects at Sea Level and at High Altitude. (Cf. Van Osta)

|  | Sea Level | Altitude | P |
|---|---|---|---|
| Diastolic BP, mm Hg | 81 ± 12 | 82 ± 17 | NS |
| Mean BP, mm Hg | 100 ± 14 | 100 ± 18 | NS |
| Systolic Vmca, cm/s | 69 ± 11 | 72 ± 18 | NS |
| Diastolic Vmca, cm/s | 34 ± 7 | 37 ± 13 | NS |
| Mean Vmca, cm/s | 49 ± 8 | 52 ± 14 | NS |
| ARI | 4.44 ± .086 | 4.55 ± 1.16 | NS |

Data are given as mean ± SD.

Table 2 depicts hypoxic thresholds for central nervous system dysfunctions at sea level and simulated altitudes causing hypoxia.

TABLE 2

Hypoxic Thresholds for CNS Dysfunction (Values derived from younger volunteers subjected to acute (minutes) decompression hypoxia. $F_iO_2$, fractional percentage of ambient oxygen. (Cf. Bailey; Butterworth; Huff; Kirkham & Datta)

| Simulated altitude (ft) | $F_iO_2$ (%) | $PaO_2$ (mm Hg) | Neurological status |
|---|---|---|---|
| Sea level | 21 | 90 | Normal |
| 5,000 | 17 | 80 | Impaired dark vision |
| 8,000-10,000 | 15-14 | 55-45 | Impaired short-term memory, difficulty learning complex tasks |
| 15,000-20,000 | 11-9 | 40-30 | Loss of judgment, euphoria, obtundation |
| >20,000 | <9 | <25 | Coma |

Retinal encephalopathies also occur at these altitudes and include torturous, leaky vasculature consistent with established physical symptoms of HACE. These are clear examples of hypoxic encephalopathies at partial pressure of oxygen; PKCg is present in samples of peripheral blood during hypoxic encephalopathies. These same oxygen pressures elicit short-term memory impairment, difficulty learning complex tasks, loss of judgment, euphoria, and obtundation.

SUMMARY OF THE INVENTION

The present invention overcomes the problems and disadvantages associated with existing neurological and psychometric assessments of cognitive, neuropsychological, and neuropsychiatric functions.

One embodiment of the invention is directed to a method for assessing an abnormality of a neurological or cognitive function of the central nervous system of a patient comprising: contacting a sample obtained from said patient with a binding partner capable of forming a complex with protein kinase C gamma (PKCg) to form a PKCg/binding partner complex; and detecting PKCg/binding partner complex formed and determining the presence of the abnormality in the neurological or cognitive function assessed.

Another embodiment is directed to a method wherein the abnormality assessed is selected from the group consisting of an abnormal behavioral, neuropsychological, or neuropsychiatric function, a movement disorder, a drug-induced or toxin-induced disorder, short-term memory loss, an encephalopathy, and combinations thereof.

Another embodiment is directed to a method wherein the abnormal neurological or cognitive function assessed is associated with chronic hypoxia. Another embodiment is directed to a method wherein the chronic hypoxia is associated with a breathing disorder, apnea, a pulmonary disorder, a surgical procedure, administration of a medication, a change in altitude or barometric pressure or a combination thereof.

Another embodiment is directed to a method wherein the abnormality assessed is not connected with an ischemic event or the restriction of blood flow to the central nervous system.

Another embodiment is directed to a method wherein the patient is a mammal. In another embodiment, the mammal is a human.

Another embodiment is directed to a method wherein the sample is a sample of peripheral blood. Another embodiment is directed to a method wherein the sample is a sample of retinal fluid.

Another embodiment is directed to a method wherein the binding partner is an anti-PKCg antibody or antibody fragment. In another embodiment, the anti-PKCg antibody is detectably labeled.

Another embodiment is directed to a method further comprising quantitatively determining the amount of PKCg/binding partner complex formed.

Another embodiment is directed to a method further comprising determining the relative amount of PKCg/binding partner complex formed as compared with the amount of PKCg/binding partner complex of a control sample indicative of a normal (non-abnormal) neurological or cognitive function.

Another embodiment is directed to a method for assessing the potential for impairment of a neurological or cognitive function of the central nervous system of a patient comprising: contacting a sample obtained from the patient with a binding partner capable of forming a binding complex with protein kinase C gamma (PKCg) to form a PKCg/binding partner complex; determining the quantity of PKCg/binding partner complex formed; and assessing the potential for impairment of the neurological or cognitive function from the quantity of PKCg/binding partner complex formed.

Another embodiment is directed to a method further comprising comparing the amount of PKCg/binding partner complex formed with an amount of PKCg/binding partner complex formed with a control sample, wherein said control sample is indicative of a known impairment of a neurological or cognitive function of the central nervous system.

Another embodiment is directed to a method further comprising monitoring the amount of PKCg/binding partner complex formed over a period of time.

Another embodiment is directed to a method for diagnosing a disorder of a neurological or cognitive function of the central nervous system of a patient comprising: contacting a sample obtained from said patient with a binding partner capable of forming a binding complex with PKCg to form a PKCg/PKCg binding partner complex, wherein detection of a PKCg/PKCg binding partner complex is diagnostic of said disorder.

Another embodiment is directed to a kit for diagnosis of a disorder of the neurological or cognitive function of the central nervous system of a patient comprising: a first substrate having immobilized thereon an anti-PKCg antibody or antibody fragment for contact with a sample obtained from the patient; a detectable label capable of binding to a PKCg/PKCg antibody complex; a second substrate which has bound thereto a PKCg/binding partner complex which is detectably labeled at a detection level that is representative of a disorder of a neurological or cognitive function of the central nervous system of a similar patient.

Another embodiment is directed to a kit further comprising a second anti-PKCg antibody reactive with another epitope of PKCg.

Another embodiment is directed to a kit wherein said first antibody is immobilized on a solid support.

Another embodiment is directed to a kit wherein the solid support is selected from the group consisting of a plastic multiwall plate, plastic or glass beads or rods, and a plastic or glass film.

Another embodiment is directed to a kit wherein the antibody or antibody fragment is labeled.

Another embodiment is directed to a kit further comprising one or more additional substrates each of which has bound thereto a PKCg/binding partner complex which is detectably labeled at a detection level that is representative of another disorder of a neurological or cognitive function of the central nervous system of a similar patient.

Other embodiments and advantages of the invention are set forth in part in the description, which follows, and in part, may be obvious from this description, or may be learned from the practice of the invention.

DESCRIPTION OF THE INVENTION

PKCg is used as a biomarker for assessing and diagnosing events related to insults resulting in interrupted cranial blood flow, such as stroke. It was surprisingly discovered that PKCg release from neural cells can be detected in peripheral blood after hypoxic events unrelated to the reduction or elimination of blood flow through affected tissues. Thus, hypoxia is a surprising and unique stimulus for the movement of PKCg from the cytoplasm to membranes in neural cells. Embodiments of this invention are generally directed to a broad range of clinical applications related to the treatment and identification of neurological functions and conditions, particularly in emergency medicine. The methods of the present invention are especially contemplated to benefit human subjects but are suitable for any mammalian subject.

One embodiment of the present invention is directed to a PKCg biological marker, which allows rapid assessment and/or identification of compromised cognitive, behavioral, neuropsychological, and/or neuropsychiatric (collectively referred to throughout as "neurological") functions under conditions associated with acute, transient hypoxia in humans.

Another embodiment is directed to assessments of cognitive, neuropsychological and/or neuropsychiatric functions employing a biological marker of hypoxia. In certain embodiments, the assessments are neurological and psychometric. Preferably, the biological marker of hypoxia is PKCg. More preferably, a diagnostically effective amount of PKCg is detected indicating, identifying, and/or distinguishing among functions of the central nervous system. In one embodiment, a sample of blood is assessed for a diagnostically effective amount of PKCg. In another embodiment, a sample of cells, preferably lysed, is assessed according to embodiments of the present invention for a diagnostically effective amount of PKCg.

Yet another embodiment is directed to a biological molecular marker, preferably one comprising PKCg, which rapidly identifies compromised neurological functions. Preferably, these functions are associated with hypoxia in humans and other mammals.

Without wishing to be bound by theory, the neurological functions, preferably related to hypoxic events, provide a specific stimulus for the movement of PKCg from the cytoplasm to membranes in neural cells. The release of PKCg from neural cells indicates a loss of normal cellular and molecular functions. This loss of normal and molecular functions underlies short- and long-term memory acquisition such as, for example, synthesis, release and metabolism of glutamate and other neurotransmitter substances as well as the regulation of gap junctions in endothelial cells of vascular tissues.

Additional embodiments facilitate categorization of and distinguishing between hypoxic encephalopathies and conditions arising from neuroanatomical/structural anomalies and/or metabolic pathologies. Such pathologies are characterized by focal metabolic changes in basal ganglia and cerebellar structures and result in disorders of movement control and coordination. Examples include the ingestion of toxic substances (e.g., alcohol), vitamin deficiencies, or adverse effects of drugs and treatments that act on central nervous system tissues.

Encephalopathies, or brain illnesses, are a significant clinical problem characterized by diffuse and complex arrays of cognitive, neuropsychological and/or psychiatric symptoms. Studies to gain insight into the underlying pathophysiology are complicated by a general lack of access to central nervous system tissues that are encased in bone and membraneous structures. Embodiments of the present invention distinguish between hypoxic encephalopathies and certain metabolic encephalopathies. Other embodiments of this invention distinguish between conditions arising from neuroanatomical/structural anomalies and/or incidental pathologies, for example, alcohol intoxication or adverse psychoactive drug effects. Additional embodiments are directed to detection and treatment of retinal encephalopathies, which afford a unique window on neurological functions, preferably functions as affected by conditions associated with hypoxia.

In another embodiment, PKCg is a molecular biomarker correlate for neurological functions as a result of conditions associated with acute, transient hypoxia. A diagnostically effective amount of PKCg is detected according to embodiments of the present invention, indicating an abnormal neurological function and/or a hypoxic event. Hypoxia can be a consequence of certain metabolic encephalopathies that result in generalized depression of cerebral function, including consciousness which may result from diminished neurocortical and other forebrain activity involved in cognition. Arousal of these structures is mediated by the ascending reticular activating system (ARAS) through thalamic synaptic relays to the neocortex. Metabolic encephalopathies result from alterations of brain chemistry at both neocortical and brainstem ARAS centers. The typical decrease in respiration would result in hypoxia. Other breathing disorders include apnea and/or chronic obstructive pulmonary disorders, surgical procedures, medications, and/or extremes of altitude and barometric pressure. The sequelae to these types of conditions are characterized by cognitive and neuropsychological dysfunctions and ataxia. A variety of treatments and established clinical protocols are presently used as interventions. The current technology for assessing short-term memory, cognitive functions or various performance tasks is based on batteries of neurological, neuropsychological and/or psychometric tests using numerous instruments. The ability to monitor the effects of established as well as novel therapeutic interventions using PKCg as a biomarker according to embodiments of the present invention facilitates diagnoses and allows for better, more effective treatments to be provided.

Surprisingly, PKCg is implicated in the underlying mechanisms of conditions characterized by hypoxia. The activation of PKCg in neural cells is additionally implicated in the molecular mechanisms of learning and behavior. In one embodiment of the present invention, determining whether PKCg in samples of peripheral blood is elevated during and/or after adverse events associated with the onset and/or recovery from acute hypoxia provides a means to assess brain function that is based on a physical, biological marker.

Oxygen is a critical consideration in the central nervous system due to the high metabolic rate, limited intrinsic energy stores and critical dependence on aerobic metabolism of the brain. Consequently, hypoxia is a well-established contributor to oxidative stress including an oxygen sensing signal cascade influenced by reactive oxygen species. The activation of phospholipases by ionic and neurotransmitter disturbances leads to the release of fatty acid and lipid co-factors that activate PKCg and facilitate its calcium-dependent translocation from the cytosol to cell membranes. Activated PKCg is implicated in the molecular processes in membranes including the regulation of tight/gap junctions and of glutamate receptors.

Arachidonic acid, alone, has been shown to activate PKCg from bovine cerebellum. The multi-enzymic oxygenase pathways mediating the synthesis of prostaglandins and other biologically active derivatives of certain essential fatty acids require molecular oxygen as they interact with other enzyme systems that act to regulate membrane integrity and mitochondrial functions that require molecular oxygen to produce the "energy currency" of cells, ATP. In addition to phospholipases and oxygenases, these include acyl-transferases, acyl-carrier proteins, elongases and desaturases as well as alpha-, beta-, and omega-degradation pathways. Certain of these components of the pathways metabolizing arachidonic and specific other essential fatty acids also produce substances with the established ability to increase the permeability of endothelial cells lining the microvasculature which would contribute to high-altitude cerebral edema, high-altitude pulmonary edema and high altitude retinal encephalopathies.

Other biomarkers of ischemia have been identified, such as S-100 and neuron-specific enolase (NSE). While a number of proteins are known to require arachidonic, diacylglycerol and/or other lipids for activation, PKCg is the only one presently identified that is unique to the central nervous system. In studies related to ischemic events, it was observed that when the blood brain barrier is compromised as a result of an ischemic event, PKCg appeared in peripheral blood. The presence of PKCg in peripheral blood is detectable in peripheral blood almost immediately following an ischemic event, and, most importantly, within the critical time window in which diagnosis and treatment of ischemic injury can prevent permanent damage to CNS tissue. PKCg is activated by a calcium- and arachidonic acid dependent association with cell membranes. PKCg slips across membranes that are compromised by diminished oxygen supplies and membranes that are leaky. Although PKCg release into the peripheral blood has been linked to ischemic events (i.e. events in which there is a restriction in blood supply), it was surprisingly discovered that PKCg can be used as a biomarker for events occurring during normal or even increased cerebral blood flow.

Performing one or more tests for ischemia using non-PKCg biomarkers in addition to assessing or detecting levels of PKCg in a sample from a subject indicates whether an ischemic event has occurred or not. A positive non-PKCg ischemic event biomarker result indicates the occurrence of an ischemic event, whereas a negative non-PKCg ischemic event biomarker result in conjunction with detection of a diagnostically effective amount of PKCg according to various embodiments of the present invention indicates a neurological function abnormality, disorder or impairment that is not associated with a transient, acute ischemic event.

Additional embodiments are directed to assessing PKCg levels in a patient at repeated time intervals; preferably, if a diagnostically effective amount of PKCg is detected, the test is repeated at 2 hour, 4 hour, 8 hour, 12 hour, 16 hour, 24 hour, and/or weekly intervals. Repeated detection of a diagnostically effective amount of PKCg is correlated to chronic hypoxia; an encephalopathy; a metabolic pathology; a metabolic encephalopathy; a neuroanatomical or structural anomaly; an impairment that is not associated with an ischemic event; a neurological dysfunction; an abnormal behavioral, neuropsychological, or neuropsychiatric function; a movement disorder; a drug-induced or toxin-induced disorder; a breathing disorder; apnea; a pulmonary disorder; a condition associated to a surgical procedure or administration of a medication; an acute and transient hypoxic event that is not connected with an ischemic event or the restriction of blood flow to the central nervous system; or combinations thereof.

Using a model of ischemic insult, middle cerebral artery occlusion (MCAO) in the rat, earlier studies have indicated that PKCg is detectable in peripheral blood samples and that the quantity directly correlates to the severity of neurological impairment in the central nervous system of the rat. Data substantiating these observations are presented in U.S. Pat. No. 6,268,223 ("Assay for Detecting Damage to the Central Nervous System" issued on Jul. 31, 2001), which is incorporated herein by reference in its entirety. Additionally, a 66% decrease in the partial pressure of oxygen in tissues before and during MCAO in the rat is associated with the presence of PKCg in peripheral blood samples. A pilot study with human samples has also been completed, and the results are consistent with the MCAO data from the rat.

Dysfunctions (such as those shown in Table 2, infra) of the central nervous system are consistent with an acute hypoxic state. Embodiments of this invention are directed to detecting PKCg, whose release from neural structures in the central nervous system, particularly the hippocampus and cerebellum, is triggered during hypoxia. Released PKCg increases in samples of peripheral blood and can be detected. Embodiments of this invention provide an index of the oxygenation of neural tissues in the central nervous system as well as the means to estimate whether cognitive, neuropsychological, neuropsychiatric and/or motor functions associated with neural tissues are adversely affected. As the technology for measuring PKCg in peripheral blood samples becomes more accessible, sensitive and miniaturized, online analysis can lead to immediate remedial efforts that can reduce or even block the impairment of central nervous system functions, particularly short-term memory loss and the anxiety of associated behavioral changes.

Embodiments of this invention have broad applications in clinical practice, particularly by emergency medical personnel.

PKCg is a specific marker for central nervous system tissue that is activated by certain fatty acid moieties such as arachidonic acid (AA). In addition, AA is the fully competent precursor of the oxygenase pathways. In the CNS, noteworthy pathways are cyclooxygenase, producing prostaglandins, thromboxanes and prostacyclins, and lipoxygenases (including 5-HETE, 12-HETE, $LTC_4$, LxA). PKCg specific for the central nervous system is not normally found in peripheral blood; however PKCg is activated during hypoxic events and/or during events related to neurological function impairment not necessarily associated with ischemia.

The amount of PKCg detected in a peripheral blood sample is proportional to the degree of neurological dysfunction; one embodiment is thus directed to quantitative assay of the PKCg in a sample to indicate the extent of impairment of or abnormality in a neurological function.

In ischemic studies, the disruption of cranial blood flow has been explained as triggering a common pathway of cell mediated damage which originates with the activation and eventual release of PKCg from neural tissues. PKCg is normally found only in the CNS and is not known to be localized to any other tissues. In the event of ischemic damage, an accompanying breakdown of the blood brain barrier has been observed, which has been explained as resulting in the release of PKCg from its normal location in the brain into venous blood. The present invention, in contrast, is directed to PKCg release during events of normal or increased blood flow. In one embodiment, the PKCg release is linked to underlying central nervous system functions; in another embodiment, PKCg release is linked to hypoxia.

Any method of detection for a diagnostically effective amount of PKCg marker is suitable for embodiments of this invention, and any known methods of detecting a specific protein in a sample may be employed. Preferably, PKCg is detected in a sample of blood, preferably in a diagnostically effective amount of PKCg, from a mammalian subject, by contacting the sample with a binding partner for PKCg, that is, a peptide, immunoglobulin, small molecule or other moiety capable of forming an association complex with PKCg. Most preferably, a diagnostically effective amount of PKCg in a sample is detected using antibodies specific for PKCg. Several such antibodies are known, and monoclonal antibodies recognizing different epitopes of PKCg are available commercially, making simple sandwich assays readily practicable. (See U.S. Pat. No. 6,268,223.)

For detection or measurement of PKCg levels in a sample, fluorescently labeled antibodies are most preferred. Many other methods of detecting PKCg directly or detecting a complex of PKCg with another moiety are known, including gas chromatography mass spectroscopy, thin layer chromatography, hydroxyl apatite chromatography, high pressure liquid chromatography, colloidal gold immunolabeling read by electron microscopy, enzyme-linked immunosorbent assays, radioactively labeled tags or antibodies specific for PKCg read using a scintillation counter, bioluminescently labeled antibodies read on a calorimeter, etc.; however, most of these methods require several hours or even days for sample preparation and/or measurement of the signal, making them inferior to sensitive fluorescence-based assays such as described in U.S. Pat. No. 6,268,223. Also, a typical detection apparatus in some cases (e.g., mass spectrophotometer, electron microscope) would not fit inside an ambulance, making performance of the assays by emergency medical personnel before a patient is brought to a hospital impossible.

In additional embodiments of the invention, the materials for detection of a diagnostically effective amount of PKCg in a sample of venous blood are conveniently assembled into a kit, so that personnel treating or transporting a patient can identify, treat and/or categorize the type of neuropsychological, behavioral and/or cognitive functions occurring in a patient's central nervous system. One kit useful for such diagnoses is based on PKCg binding and is capable of providing multiple levels of detection and quantitation. The level of detection provides quantitative assessment of neurological function based on calibration of fluorescently tagged antibodies to PKCg detected in venous blood.

Another embodiment is directed to correlating retinal physiology with central nervous system functions. Preferably, assessment of retinal vasculature is performed via retinography or similar technologies; more preferably, such assessment is correlated with the release of PKCg from the central nervous system. Such release of PKCg is correlated to a hypoxic event, a metabolic encephalopathy, a central nervous system anomaly, or combinations thereof.

In addition to providing rapid diagnosis of a hypoxic event by emergency and medical personnel, the methods and kits described herein also may be used to detect a diagnostically effective amount of PKCg and to monitor PKCg levels as part of a routine checkup procedure or to monitor general functions and conditions of the central nervous system. In one embodiment, a PKCg monitor functions similarly to a glucometer.

Other embodiments and uses of the invention will be apparent to those skilled in the art from consideration of the specification and practice of the invention disclosed herein. All references cited herein, including U.S. Provisional Application No. 60/886,532 to which the present application claims the benefit of priority, all publications, U.S. and foreign patents and patent applications, are specifically and entirely incorporated by reference. The term "comprising" as used throughout this application includes the more limiting terms and phrases "consisting essentially of" and "consisting." It is intended that the specification and examples be considered exemplary only with the true scope and spirit of the invention indicated by the following claims.

The invention claimed is:

1. A method for assessing an abnormality of a neuropsychological or cognitive function of the central nervous system of a patient comprising: contacting a sample obtained from said patient with a binding partner capable of forming a complex with protein kinase C gamma (PKCg) to form a PKCg/binding partner complex; and detecting PKCg/binding partner complex tanned and determining the presence of the abnormality in the neuropsychological or cognitive function assessed, the abnormal neuropsychological or cognitive function being associated with hypoxia and not connected with an ischemic event or the restriction of blood flow to the central nervous system.

2. The method of claim 1, wherein the abnormality is selected from the group consisting of an abnormal behavioral, neuropsychological, or neuropsychiatric function, a movement disorder, a drug-induced or toxin-induced disorder, short-term memory loss, an encephalopathy, and combinations thereof.

3. The method of claim 1, wherein the hypoxia is associated with a breathing disorder, apnea, a pulmonary disorder, a surgical procedure, administration of a medication, a change in altitude or barometric pressure or a combination thereof.

4. The method of claim 1, wherein the patient is a mammal.

5. The method of claim 4, wherein the mammal is a human.

6. The method of claim 1, wherein the sample is a sample of peripheral blood.

7. The method of claim 1, wherein the sample is a sample of retinal fluid.

8. The method of claim 1, wherein the binding partner is an anti-PKCg antibody or antibody fragment.

9. The method of claim 1, wherein said anti-PKCg antibody is detectably labeled.

10. The method of claim 1, further comprising quantitatively determining the amount of PKCg/binding partner complex formed.

11. The method of claim 1, further comprising determining the relative amount of PKCg/binding partner complex formed as compared with the amount of PKCg/binding partner complex of a control sample indicative of a normal neurological neuropsychological or cognitive function.

12. The method of claim 1, wherein the patient's blood has a partial pressure of oxygen ($PaO_2$) of between about 25 mm Hg and 80 mm Hg.

13. The method of claim 12, wherein the hypoxia is associated with a condition selected from the group consisting of: altitude sickness, high altitude pulmonary edema (HAPE), high altitude cerebral edema (HACE), retinal encephalopathy, and hypoxic encephalopathy.

14. The method of claim 12, wherein the hypoxia is associated with one selected from the group consisting of: a breathing disorder, apnea, a pulmonary disorder, a surgical procedure, administration of medication, a change in altitude and a change in barometric pressure.

* * * * *